United States Patent [19]

Saari

[11] Patent Number: 4,942,226
[45] Date of Patent: Jul. 17, 1990

[54] HALOGENATED PYRIMIDINE NUCLEOSIDES AND THEIR DERIVATIVES

[75] Inventor: Walfred S. Saari, Lansdale, Pa.

[73] Assignee: Merck & Co., Inc., Rahway, N.J.

[21] Appl. No.: 291,714

[22] Filed: Dec. 29, 1988

[51] Int. Cl.$^5$ ................. C07H 19/073; A61K 31/505; A61K 31/195; A61K 31/215

[52] U.S. Cl. ...................................... 536/23; 514/917; 562/553

[58] Field of Search ...................... 514/49, 917; 536/23

[56] References Cited

U.S. PATENT DOCUMENTS 4,603,133 7/1986 Engelhardt et al. ................. 514/229
4,731,369 3/1988 Engelhardt et al. ................. 514/327

OTHER PUBLICATIONS

Coleman, *Journal of the National Cancer Institute* vol. 80, No. 5 pp. 310-317 (1988).

*Primary Examiner*—John W. Rollins
*Assistant Examiner*—Gary L. Kunz
*Attorney, Agent, or Firm*—Richard S. Parr; Charles M. Caruso

[57] ABSTRACT

Halogenated pyrimidine nucleoside derivatives with improved aqueous solubility and methods of enhancing the concentration of drugs in malignant tumors and promoting uniform distribution of the drug throughout the tumor. These basic and hydrophilic ester prodrugs are designed to undergo conversion to the active drug by an intramolecular chemical reaction at practical rates under physiological conditions.

9 Claims, No Drawings

HALOGENATED PYRIMIDINE NUCLEOSIDES AND THEIR DERIVATIVES

BACKGROUND OF THE INVENTION

Halogenated pyrimidine nucleosides are clinically effective radiosensitizers. These nucleosides replace thymidine in the DNA of cycling cells rendering them more sensitive to radiation compared to cells not containing halogenated pyrimidines. Kinsella, et al. *Int. J. Radiation Oncology Biol. Phys.*, vol. 10, pp. 1399–1406 (1984), and Mitchell et al., *Int. J. Radiation Oncology Biol. Phys.*, Vol. 12, pp. 1513–1518 (1986) describe the use of these radiosensitizers in radiobiology and radiotherapy.

Kinsella, et al. review the basic strategy for using halogenated pyrimidine analogs bromodeoxyuridine and iododeoxyuridine as radiosensitizers, and describe clinical trials using these compounds. Recent clinical trials using continuous intravenous administration show that systemic toxicity limits the infusion rate and duration of infusion. The authors conclude that therapeutic gain must be improved by limiting systemic toxicity and increasing tumor cell incorporation.

Mitchell, et al. review halogenated pyrimidine non-hypoxic cell radiosensitizers incorporated into cellular DNA for X-ray sensitization. Recent studies in high-grade glioblastoma and large unresectable sarcoma tumor sites show the compounds have little impact on long-term survival (Kinsella et al., *J. Clin. Oncol.* vol. 2 pp. 1144–1150 (1984) and Kinsella et al. *Int. J. Radiat. Oncol. Biol. Phys.* vol. 10, pp. 69–76 (1984)).

Previous ester prodrugs have depended on enzymatic hydrolysis to give useful rates of conversion of prodrugs to drugs. There is great variability in esterase concentrations between individuals and tumor drug levels may be inconsistent and unpredictable.

It is a purpose of the invention to provide halogenated pyrimidine nucleosides which replace DNA thymidine bases with halogenated bases to an extent sufficient to deliver a high degree of radiosensitization.

It is also a purpose of the invention to provide prodrugs that undergo transformation by a non-enzymatic mechanism and produce more predictable and consistent tumor levels of drug.

It is also a purpose of the invention to provide halogenated pyrimidine nucleosides which can be safely delivered to malignant cells at high concentration.

It is also a purpose of the invention to provide safe methods for replacing DNA thymidine base with halogenated bases, thereby delivering a high degree of radiosensitization.

DESCRIPTION OF THE INVENTION

The invention includes halogenated pyrimidine nucleoside derivatives with improved aqueous solubility and methods of enhancing the concentration of drugs in malignant tumors and promoting uniform distribution of the drug throughout the tumor. Compounds of the invention include:

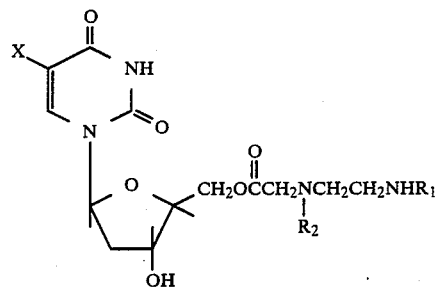

wherein

X is a halogen, e.g. fluorine, chlorine, bromine or iodine;

$R_1$ is hydrogen, a $C_1$–$C_6$ alkyl group, or a $C_5$–$C_7$ cycloalkyl ethyl group; and $R_2$ is hydrogen or a $C_1$–$C_6$ alkyl group.

and

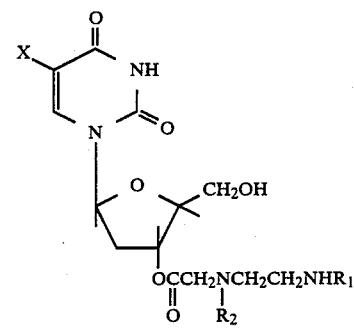

wherein X, $R_1$ and $R_2$ are as defined above.

These basic and hydrophilic ester prodrugs, in contrast to those prodrugs that depend on enzymatic conversion to the active molecule, are designed to undergo conversion to the active drug by an intramolecular chemical reaction at practical rates under physiological conditions. The prodrugs of the invention contain an N-aminoalkyl or N-alkylaminoalkyl aminoester moiety which is stable in protonated form, and yet undergoes an intramolecular condensation or elimination reaction wherein the terminal amino group displaces the alcoholic moiety of the ester function at physiological pH. As a result, the less basic and more lipophilic (relative to the prodrug) active drug is released.

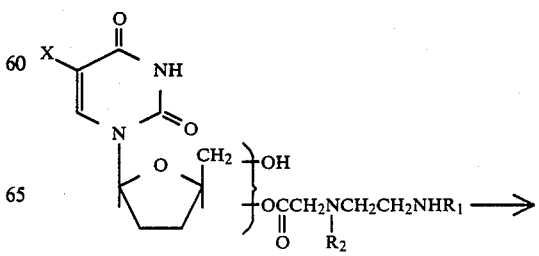

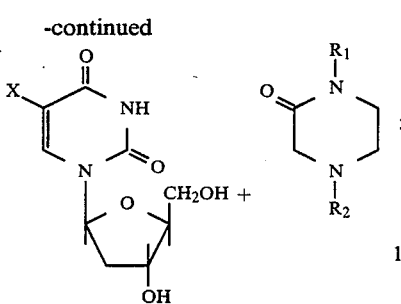

The ester prodrug is preferably administered by the intravenous or intra-arterial route at a rate which will maximize tumor levels of halogenated pyrimidine without unduly stressing the patient. The drug may be administered either by continuous infusion or in a series of injections.

The dose of the prodrug administered, whether intravenously, intra-arterially, orally or topically, and whether a single dose or a daily dose, will, of course, vary with the needs of the individual. Such factors as body weight of the patient, severity of the disease, and other physical conditions of the patient figure prominently in the determination of dosage and means of administration. Other considerations include the rate of conversion of a given ester to the alcohol in the plasma and in the particular tumor type under treatment, as well as the rate of elimination of prodrug and alcohol from the body. In this manner, both the rate of administration and the total dose given will be determined by the prescribing physician based upon his clinical judgement. The useful dosage range for a course of such treatments is between 1 mg and 100 mg per kg of body weight per day.

The dosage form for intravenous or intra-arterial administration is a sterile, isotonic solution of the drug. Oral dosage forms such as tablets, capsules or elixers may also be used whenever appropriate. Capsules or tablets containing 25, 50, 100 or 500 mg of drug per capsule or tablet are satisfactory.

Compounds of the invention may be prepared by one of the methods outlined below.

According to one procedure, the 5'-tosylate is displaced by the sodium salt of the tert-butyloxycarbonyl (Boc-) protected diaminoacid followed by deprotection.

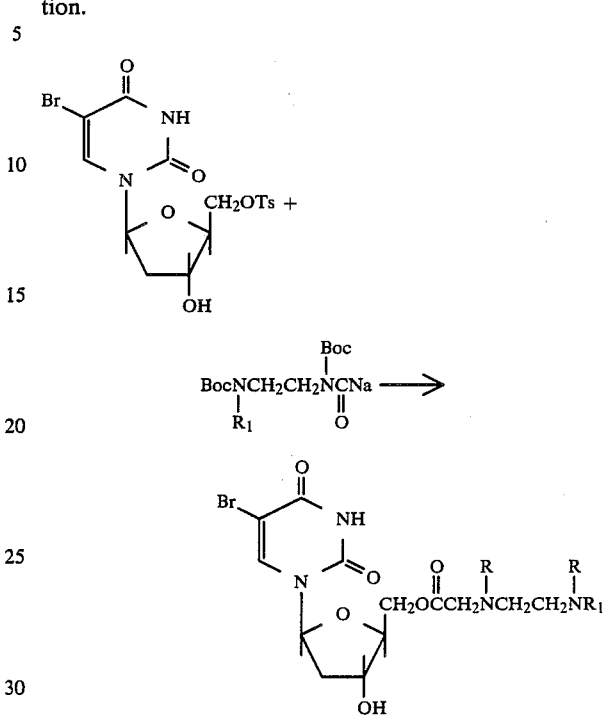

where
R = Boc, H; and
$R_1$ = hydrogen, a $C_1$–$C_6$ alkyl group, or a $C_5$–$C_7$ cycloalkyl ethyl group.

Another procedure involves esterification of unprotected pyrimidine nucleoside with Boc protected active ester followed by deprotection. This method gives mixtures of the two possible mono esters and diester.

A preferred procedure involves esterification of the pyrimidine nucleoside in which one of the two sugar alcohol functions is protected with a trityl group, and then removal of the protective groups.

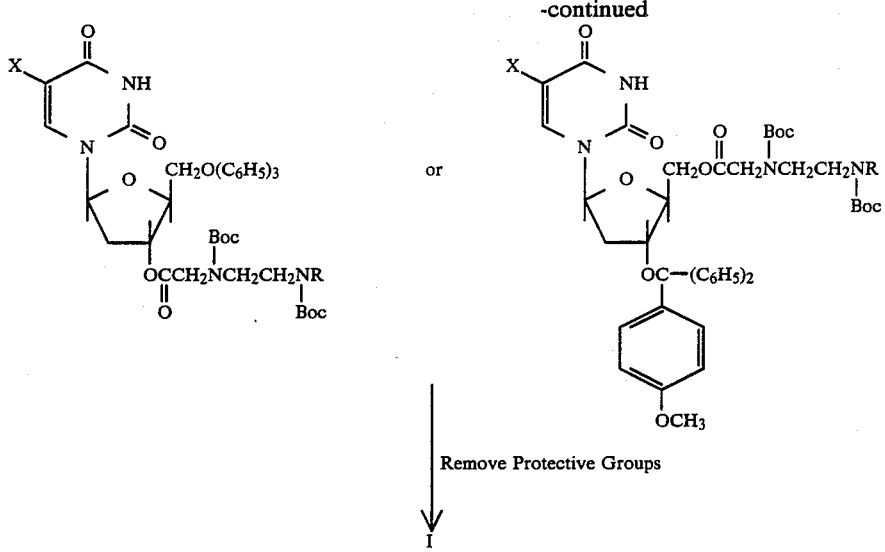

Remove Protective Groups

R and X are as defined above.

The following examples are intended to illustrate but do not limit the process of preparation, product, compositions, or method of treatment aspects of the invention. Temperatures are in degrees Celsius unless otherwise indicated throughout the application.

EXAMPLE 1

5-Bromo-2'-deoxyuridine 3'-N-(2-Ethylaminoethyl)-glycyl Ester Dihydrochloride

Step. 1 N-(2-Ethylaminoethyl)glycine.

A solution of glyoxylic acid hydrate (9.2 g, 0.10 mol) and N-ethylethylenediamine (8.82 g, 0.10 mol) in ethanol (150 ml) was hydrogenated in a Paar apparatus at 20°–25° and an initial pressure of 51 psi with 5% Pd on carbon (2.0 g) as catalyst. After 18 hours, hydrogen uptake was complete. Catalyst was removed by filtration through a pad of diatomaceous earth and the filtrate concentrated to give N-(2-ethylaminoethyl)glycine.

Step. 2 N-(1,1-Dimethylethoxycarbonyl)-N-[2-[N-(1,1-dimethylethoxycarbonyl)-N-ethylamino]-ethyl]glycine.

A solution of N-(2-ethylaminoethyl)glycine (14.6 g, 0.10 mol) in water (150 ml) and THF (100 ml) containing sodium hydroxide (4.0 g, 0.10 mol) was stirred at room temperature while a solution of di tert. butyl dicarbonate (48.0 g, 0.22 mol) in THF (100 mL) was added over 1 hour. After stirring at room temperature for 18 hours, THF was removed under reduced pressure and the aqueous portion extracted with diethyl ether. The aqueous phase was then acidified with citric acid and extracted with two portions of methylene chloride. The combined organic extracts were dried (Na2SO4), filtered and concentrated. Flash chromatography over silica gel and elution with 20% methanol-80% chloroform gave 25.9 g of product.

Step 3. N-(1,1-Dimethylethoxycarbonyl)-N-[2-[N-(1,1-dimethylethoxycarbonyl)-N-ethylamino]-ethyl]glycine N-Hydroxysuccinimide Ester.

A solution of the protected acid from Step 2 (25.9 g, 74.8 mmol) and N-hydroxysuccinimide (9.75 g, 82.1 mmol) in methylene chloride (350 mL) and DMF (17 ml) was cooled in an ice bath while a solution of 1-cyclohexyl-3-(2-morpholinoethyl) carbodiimide metho-p-toluenesulfonate (34.8 g, 82.1 mmol) in methylene chloride (250 mL) was added over 75 minutes. After stirring in the ice bath for 1 hour and then at room temperature for 18 hours, the reaction mixture was washed successively with water, 10% citric acid, saturated sodium bicarbonate solution, water and then dried (Na2SO4). The filtered solution was concentrated under reduced pressure and the residue recrystallized from ethyl acetate-hexane to give 17.7 g of product, mp 116°–119°.

Step 4. 5-Bromo-2'-deoxyuridine 3'-N-(1,1-Dimethylethoxycarbonyl)-N-[2-[N-(1,1-dimethylethoxycarbonyl)-N-ethylamino]ethyl]glycyl ester.

A solution of the hydroxysuccinimide ester from Step 3 (723 mg, 1.63 mmol), (+) 5-bromo-2'-deoxyuridine (500 mg, 1.63 mmol) and 4-dimethylaminopyridine (199 mg, 1.63 mmol) in acetonitrile (30 ml) and DMF (5 mL) was stirred under N2 at room temperature for 5 days. After concentrating under reduced pressure, the residue was flash chromatographed over silica gel. Elution with 2% methanol-98% chloroform gave 0.17 g of product.

Step 5. 5-Bromo-2'-deoxyuridine 3'-N-(2-Ethylaminoethyl)glycylester Dihydrochloride A solution of the protected ester from Step 4 (0.17 g) in ethyl acetate (10 mL) was cooled in an ice bath and saturated with HCl gas for 5 minutes. After stirring in the ice bath for 30 minutes, solvents were removed under reduced pressure and the residue recrystallized from methanol-ethylacetate hexane to give 66 mg of product, mp 208°–09° dec., soften at 203°.

Calcd. for $C_{15}H_{23}BrN_4O_6 \cdot 2HCl$: C, 35.45, H, 4.96, N, 11.02. Found: C, 35.25, H, 5.06, N, 10.72.

EXAMPLE 2

5-Bromo-2'-deoxyuridine 3'-[N-(2-(2-Cyclohexylethylamino)ethyl)glycyl]ester Dihydrochloride Step 1. N-(2-(2-Cyclohexylethylamino)ethyl)glycine.

A solution of N-(2-cyclohexyethyl) ethylenediamine (8.52 g, 50 mmol) and glyoxylic acid hydrate (4.7 g, 50 mmol) in ethanol (200 mL) and water (30 mL) was hydrogenated in a Paar apparatus at 20°–25° and an initial pressure of 39 psi over 5% Pd on carbon catalyst. After hydrogen uptake was complete, catalyst was removed by filtration and the filtrate concentrated to give the diaminoacid.

Step 2. N-(1,1-Dimethylethoxycarbonyl)-N-[2-(N-(1,1-dimethylethoxycarbonyl)-2-cyclohexyethylamino)ethyl]glycine.

A solution of N-(2-(2-cyclohexyethylamino)-ethyl)glycine (2.67 g, 11.7 mmol) in water (10 mL), THF (15 mL) and 1N NaOH (12 mL) was stirred at room temperature while a solution of di-tert. butyl dicarbonate (5.46 g, 25 mmol) in THF (10 mL) was added over 30 minutes. After stirring at room temperature for 20 hours, THF was removed under reduced pressure and the aqueous solution acidified with citric acid. Product was extracted into ethyl acetate which was then washed with brine, dried ($Na_2SO_4$), filtered and concentrated. The residue was flash chromatographed over silica gel and pure product (4.9 g) eluted with 20% methanol-80% chloroform.

Step 3. N-(1,1-Dimethylethoxycarbonyl)-N-[2-(N-(1,1-dimethylethoxycarbonyl)-2-cyclohexylethylamino)ethyl]glycine N-Hydroxysuccinimide Ester A solution of the protected acid from Step 2 (4.0 g, 9.33 mmol), N-hydroxysuccinimide (1.1 g, 9.33 mmol) and 1-cyclohexyl-3-(2-morpholinoethyl)-carbodiimide metho-p-toluenesulfonate (3.95 g, 9.33 mmol) in methylene chloride (105 mL) was stirred at room temperature for 20 hours. After washing with 10% citric acid and water, the organic layer was dried ($Na_2SO_4$), filtered and concentrated to give 2.9 g of the ester. An analytical sample, mp 121.0°–123.0°, was obtained upon recrystallization from ethyl acetate-hexane.

Calcd. for $C_{26}H_{43}N_3O_8$: C, 59.41; H, 8.25; N, 7.99. Found: C, 59.37; H, 8.47; N, 7.71.

Step 4. 5-Bromo-5'-trityl-2'-deoxyuridine

A solution of (+) 5-bromo-2'-deoxyuridine (5.0 g, 16.3 mmol) and trityl chloride (5.6 g, 20 mmol) in pyridine (50 mL) was stirred at 120° for 1 hour, cooled and then concentrated under reduced pressure. After adding water to the residue, product was extracted into methylenechloride which was then dried ($Na_2SO_4$), filtered and concentrated. The residue was flash chromatographed over silica gel and product eluted with 20% methanol-80% chloroform. Recrystillization from ethyl acetate-hexane gave analytically pure trityl derivative as the ethyl acetate solvate (4.25 g), mp 143°–45° soften at 110°–15°.

Calcd. for $C_{28}H_{25}BrN_2O_5 \cdot \frac{1}{3} C_4H_8O_2$: C, 60.71; H, 4.93; N, 4.72. Found: C, 60.84; H, 5.32; N, 4.63.

Step 5. 5-Bromo-5'-trityl-2'-deoxyuridine 3'-N-(1,1-Dimethylethoxycarbonyl)-N-[2-(N-(1,1-dimethylethoxycarbonyl)-2-cyclohexylethylamino)-ethyl]glycyl Ester.

A solution of the hydroxysuccinimide ester from Step 3, Example 2 (0.89 g, 1.69 mmol), 5-bromo-5'-trityl-2'-deoxyuridine (1.0 g, 1.69 mmol) and 4-dimethylaminopyridine (0.21 g, 1.69 mmol) in acetonitrile (50 mL) was stirred under $N_2$ at room temperature for 45 hours. An additional 0.45 g of hydroxysuccinimide ester was then added and stirring continued for 20 hours more. After concentrating under reduced pressure, the residue was flash chromatographed over silica gel. Elution with 2% methanol-98% methylene chloride gave 1.3 g of product.

Step 6. 5-Bromo-2'-deoxyuridine 3'-[N-(1,1-Dimethylethoxycarbonyl)-N-2-(N-(1,1-dimethylethoxycarbonyl)-2-cyclohexylethylamino)ethyl]-glycyl Ester.

A solution of the trityl derivative from Step 5, Example 2 (1.3 g) in 80% acetic acid-water (30 ml) was stirred at 60° for 2 hours. After concentrating under reduced pressure, the residue was partitioned between chloroform and water. The organic extract was washed with water, dried ($Na_2SO_4$), filtered and concentrated. Flash chromatography over silica gel and elution with 3% methanol-97% chloroform gave 0.50 g of product.

Step 7. 5-Bromo-2'-deoxyuridine 3'-N-(2-(2-cyclohexylethylamino)ethyl)glycyl Ester dihydrochloride.

A solution of the BOC protected ester from Step 6 (0.50 g) in ethyl acetate (20 mL) was cooled in an ice bath and saturated with HCl gas for 5 minutes. After stirring at ice bath temperature for 15 minutes and then at room temperature for 30 minutes, solvent was removed under reduced pressure and the residue recrystallized from methanol-ethyl acetate-hexane to give 0.31 g of product, mp 142°–52° dec.

Calcd. for $C_{21}H_{33}BrN_4O_6 \cdot 2$ HCl: C, 41.46; H, 6.13; N, 9.21. Found: C, 41.03; H, 6.11; N, 8.98.

EXAMPLE 3

5-Bromo-2'-deoxyuridine 5'-N-(2-(2-cyclohexylethylamino)ethyl]glycyl Ester Dihydrochloride.

Step 1. 5-Bromo-5'-isobutyloxycarbonyl-2'-deoxyuridine

Isobutylchloroformate (2.32 g, 17 mmol) was added over 3 minutes to a stirred solution of (+) 5-bromo-2'-deoxyuridine (5.0 g, 16.3 mmol) in pyridine (100 mL) cooled in an ice bath. After stirring at room temperature for 18 hours, solvent was removed under reduced pressure and the residue flash chromatographed over silica gel. Elution with 5% methanol-95% chloroform gave 4.3 g of product. An analytical sample, mp 119°–21°, was obtained by recrystallization from ethyl acetate-hexane.

Calcd. for $C_{14}H_{19}BrN_2O_7$: C, 41.29; H, 4.70; N, 6.88. Found: C, 41.06; H, 4.75; N, 6.77.

Step 2. 5-Bromo-5'-isobutyloxycarbonyl-3'-(4-methoxytrityl)-2'-deoxyuridine

A solution of 5-bromo-5'-isobutyloxycarbonyl-2'-deoxyuridine (4.2 g, 10.3 mmol) and 4-methoxyphenyl diphenylmethylchloride (3.4 g, 11 mmol) and pyridine (75 mL) was stirred at 100° for 3 hours. Solvent was removed under reduced pressure and the residue partitioned between ethyl acetate and water. The ethyl acetate extract was washed with brine, dried ($Na_2SO_4$), filtered and concentrated. Flash chromatography over silica gel and elution with 20% ethylacetate-80% n-butyl chloride gave 4.7 g of product.

Step 3. 5-Bromo-3'-(4-methoxytrityl)-2'-deoxyuridine

A solution of the carbonate from Step 2 (4.7 g, 6.92 mmol) in dioxane (35 mL) containing water (8 mL) and 1N NaOH (27.6 mL) was stirred at room temperature for 90 minutes. Citric acid was added to adjust the pH to 7.5 and product extracted with two portions of chloroform. The chloroform extracts were combined, dried ($Na_2SO_4$), filtered and concentrated. The residue was flash chromatographed over silica gel. Elution with 2% methanol-98% chloroform gave 2.6 g of product.

Step 4. 5-Bromo-3'-(4-methoxytrityl)-2'-deoxyuridine 5'-N-(1,1-Dimethylethoxycarbonyl)-N-[2-(N-1,1-dimethylethoxycarbonyl-2-cyclohexyethylamino)ethyl]glycyl Ester A solution of the protected alcohol of Step 3 (1.9 g, 3.20 mmol), N-(1,1-dimethylethoxycarbonyl)-N-[2-(N-1,1-dimethylethoxycarbonyl-2-cyclohexylethylamino)ethyl]glycine (1.37 g, 3.20 mmol) and 4- dimethylaminopyridine (0.78 g, 6.40 mmol) in methylene chloride (50 mL) was cooled in an ice bath under N₂ while a solution of dicyclohexylcarbodiimide (0.66 g, 3.20 mmol) in methylene chloride (15 mL) was added over 20 minutes. After stirring at room temperature for 18 hours, chloroform was added and the reaction mixture washed with 10% citric acid, saturated sodium bicarbonate solution and water. The organic extract was dried (Na₂SO₄), filtered and concentrated and the flash chromatographed over silica gel. Elution with 2% methanol-98% chloroform gave 3.3 g of product.

Step 5. 5-Bromo-2'-deoxyuridine 5'-N-(1,1-Dimethylethoxycarbonyl)-N-[2-(N-(1,1-dimethylethoxycarbonyl)-2-cyclohexylethylamino)ethyl]glycyl Ester A solution of the protected ester from Step 4 (3.3 g) in 80% acetic acid-water (100 mL) was stirred at 60° for 90 minutes. After concentrating under reduced pressure, the residue was partitioned between ethyl acetate and saturated sodium bicarbonate solution. The ethyl acetate extract was washed with brine two times, dried (Na₂SO₄), filtered and concentrated. Flash chromatography of the residue over silica gel and elution with 3% methanol-97% chloroform gave 1.3 g of product.

Step 6. 5-Bromo-2'-deoxyuridine-5'-N-(2-(2-cyclohexylethylamino)ethyl)glycyl Ester Dihydrochloride A solution of the protected ester from Step 5. (1.3 g) in ethyl acetate (25 mL) was cooled in an ice bath and saturated with HCl gas for 8 minutes. After stirring in the ice bath for 15 minutes and then at room temperature for 30 minutes, solvent was removed under reduced pressure and the residue recrystallized from methanol-ethyl acetate to give 0.94 g of product, mp 168°-76° dec.

Calcd. for $C_{21}H_{33}BrN_4O_6 \cdot 2HCl$ C, 42.72, H, 5.98, N, 9.49. Found: 42.45, 6.36; N, 9.69

EXAMPLE 4

Determination of Ester Half-lives

Two mL of phosphate buffer preheated to 37° were added to approximately 0.5 mg of the ester dihydrochloride. The resulting solution was heated at 37° while 20 μL samples were removed at intervals and injected directly into the HPLC injection port.

Unreacted ester and 5-halo-2'-deoxyuridine concentrations were determined by HPLC analysis on a C-18 reverse phase column using a gradient of 98% pH 2.4 phosphoric acid—2% acetonitrile to 70% pH 2.4 phosphoric acid—30% acetonitrile over 10 minutes. The UV detector was set at 280 nm. The half-life ($t_{\frac{1}{2}}$) is the time required for 50% conversion of ester to alcohol.

TABLE I

| Compound | $t_{\frac{1}{2}}$, min. 37° | |
|---|---|---|
| | pH 7.4 | pH 6.8 |
| Br-uridine-CH₂OH, O₂CCH₂NHCH₂CH₂NHC₂H₅ | 26 | 32 |
| Br-uridine-CH₂OH, O₂CCH₂NHCH₂CH₂NHCH₂CH₂-cyclohexyl | 29 | 47 |
| Br-uridine-CH₂O₂CCH₂NHCH₂CH₂NHCH₂CH₂-cyclohexyl, OH | 22 | 35 |

What is claimed is:

1. A compound of the formula:

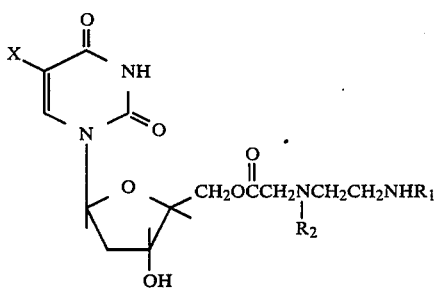

wherein
X is a halogen;
$R_1$ is hydrogen, a $C_1$–$C_6$ alkyl group, or a $C_5$–$C_7$ cycloalkyl ethyl group; and
$R_2$ is hydrogen or a $C_1$–$C_6$ alkyl group.

2. A compound of the formula:

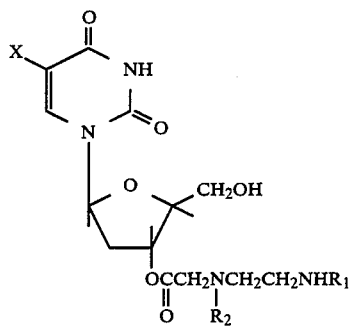

wherein
X is a halogen;
$R_1$ is hydrogen, a $C_1$–$C_6$ alkyl group, or a $C_5$–$C_7$ cycloalkyl ethyl group; and
$R_2$ is hydrogen or a $C_1$–$C_6$ alkyl group.

3. A compound of claim 1 which is 5-bromo-2'-deoxyuridine 5'-N-(2-ethylaminoethyl)-glycylester.

4. A compound of claim 1 which is 5-bromo-2'-deoxyuridine 5'-N-(2-(2-cyclohexylethylamino)ethyl)glycylester.

5. A compound of claim 2 which is 5-bromo-2'-deoxyuridine 3'-N-(2-(2-cyclohexylethylamino)ethyl)glycylester.

6. A pharmaceutical composition for enhancing the therapeutic effect of radiation which consists of an effective amount of a compound recited in claim 1.

7. A pharmaceutical composition for enhancing the therapeutic effect of radiation which consists of an effective amount of a compound recited in claim 2.

8. A method of enhancing the bioavailability of a compound of the formula:

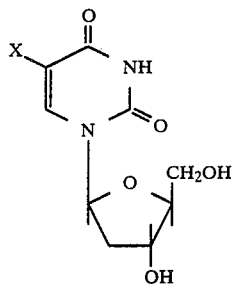

wherein X is a halogen, which comprises administering to a patient a compound of the formula:

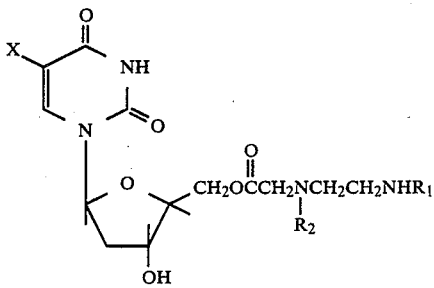

wherein:
X is a halogen;
$R_1$ is hydrogen, a $C_1$–$C_6$ alkyl group, or a $C_5$–$C_7$ cycloalkyl ethyl group; and
$R_2$ is hydrogen or a $C_1$–$C_6$ alkyl group.

9. A method of enhancing the bioavailability of a compound of the formula:

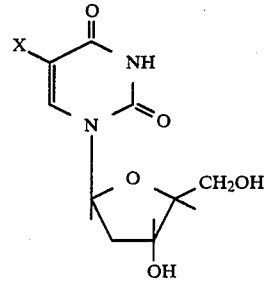

wherein X is a halogen, which comprises administering to a patient a compound of the formula:

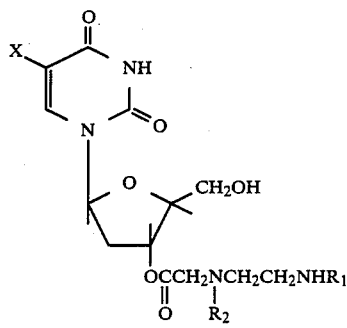

wherein:
X is a halogen;
$R_1$ is hydrogen, a $C_1$–$C_6$ alkyl group, or a $C_5$–$C_7$ cycloalkyl ethyl group; and
$R_2$ is hydrogen or a $C_1$–$C_6$ alkyl group.

* * * * *